(12) United States Patent
Lahtivuori et al.

(10) Patent No.: US 10,845,973 B2
(45) Date of Patent: Nov. 24, 2020

(54) BREATHING APPARATUS AND METHOD FOR USER INTERACTION THEREWITH

(75) Inventors: Madlene Lahtivuori, Johanneshov (SE); Anette Sunna, Stockholm (SE); Helena Stone, Bromma (SE)

(73) Assignee: MAQUET CRITICAL CARE AB, Solna (SE)

( * ) Notice: Subject to any disclaimer, the term of this patent is extended or adjusted under 35 U.S.C. 154(b) by 214 days.

(21) Appl. No.: 14/405,027

(22) PCT Filed: Jun. 3, 2012

(86) PCT No.: PCT/EP2012/060454
§ 371 (c)(1),
(2), (4) Date: Jan. 13, 2015

(87) PCT Pub. No.: WO2013/182218
PCT Pub. Date: Dec. 12, 2013

(65) Prior Publication Data
US 2015/0160845 A1   Jun. 11, 2015

(51) Int. Cl.
*H04N 5/445* (2011.01)
*A61N 1/362* (2006.01)
(Continued)

(52) U.S. Cl.
CPC ........ *G06F 3/04847* (2013.01); *G06F 3/0488* (2013.01); *G06F 3/04842* (2013.01);
(Continued)

(58) Field of Classification Search
CPC .............. G06F 3/04883; G06F 3/0488; G06F 3/04886; A61M 16/0051; A61B 5/08
See application file for complete search history.

(56) References Cited

U.S. PATENT DOCUMENTS 5,669,379 A   9/1997   Somerson et al.
5,915,379 A * 6/1999   Wallace .............. G06F 3/04842
                                                                            128/204.21
(Continued)

FOREIGN PATENT DOCUMENTS

EP        0 901 798 A1    3/1999
EP          1205837 A2    5/2002
(Continued)

OTHER PUBLICATIONS

Office Action issued in counterpart JP Application No. 2015-514367, dated Sep. 10, 2018.
(Continued)

*Primary Examiner* — Jordany Nunez
(74) *Attorney, Agent, or Firm* — Wesley Scott Ashton; Kevin Godlewski

(57) ABSTRACT

A breathing apparatus has one or more electronic processors and a touch screen communicatively coupled to at least one of the processors. The processor is configured to provide a user interface on the touch screen for modification of at least one operational parameter of the breathing apparatus. The user interface includes at least two touch sensitive display areas on the display area of the touch screen for modification of the operational parameter by an operator of the breathing apparatus. Each of the two touch sensitive display areas is dedicated for different types of user interaction, i.e. different user interaction modes are provided for by each of the two different display areas.

17 Claims, 12 Drawing Sheets

(51) Int. Cl.
*G06F 3/048* (2013.01)
*G06F 3/0484* (2013.01)
*G16H 40/63* (2018.01)
*G16H 20/40* (2018.01)
*G06F 3/0488* (2013.01)
*A61M 16/00* (2006.01)
*A61B 5/08* (2006.01)

(52) U.S. Cl.
CPC ............ *G16H 20/40* (2018.01); *G16H 40/63* (2018.01); *A61B 5/08* (2013.01); *A61M 16/0051* (2013.01); *G06F 3/04883* (2013.01); *G06F 3/04886* (2013.01)

(56) References Cited

U.S. PATENT DOCUMENTS

| | | | |
|---|---|---|---|
| 2003/0125776 A1* | 7/2003 | Turney | A61N 1/37247 607/27 |
| 2003/0210286 A1 | 11/2003 | Gerpheide et al. | |
| 2004/0158132 A1 | 8/2004 | Zaleski | |
| 2005/0030292 A1* | 2/2005 | Diederiks | G09B 21/003 345/173 |
| 2005/0051167 A1* | 3/2005 | Biondi | A61M 16/00 128/204.21 |
| 2007/0013662 A1 | 1/2007 | Fauth | |
| 2008/0000477 A1 | 1/2008 | Huster et al. | |
| 2008/0072896 A1 | 3/2008 | Setzer et al. | |
| 2009/0022338 A1 | 1/2009 | Wong et al. | |
| 2009/0228828 A1* | 9/2009 | Beatty | G06F 3/0488 715/786 |
| 2010/0011307 A1* | 1/2010 | Desfossez | A61M 16/0051 715/764 |
| 2010/0134425 A1* | 6/2010 | Storrusten | G06F 3/0425 345/173 |
| 2010/0269824 A1 | 10/2010 | Friberg et al. | |
| 2010/0293496 A1* | 11/2010 | Lafferty | A61M 5/14546 715/772 |
| 2010/0315345 A1 | 12/2010 | Laitinen | |
| 2011/0224523 A1* | 9/2011 | Budiman | A61B 5/14532 600/365 |
| 2011/0265024 A1* | 10/2011 | Leone | A61M 16/0051 715/771 |
| 2012/0055479 A1 | 3/2012 | Friberg et al. | |
| 2013/0055134 A1* | 2/2013 | Knor | A61M 16/0051 715/771 |
| 2013/0066472 A1* | 3/2013 | Harrod | G05B 19/042 700/276 |
| 2013/0112202 A1* | 5/2013 | Fogelbrink | A61M 16/00 128/204.21 |
| 2015/0301728 A1 | 10/2015 | Onozuka et al. | |

FOREIGN PATENT DOCUMENTS

| | | |
|---|---|---|
| GB | 2307383 A | 5/1997 |
| JP | H09198224 | 7/1997 |
| JP | H11114066 A | 4/1999 |
| JP | 2001515386 A | 9/2001 |
| JP | 2002163052 A | 6/2002 |
| JP | 2004243126 A | 9/2004 |
| JP | 2006297087 A | 11/2006 |
| JP | 200990141 A | 4/2009 |
| JP | 2010-146089 A | 7/2010 |
| JP | 2010146089 A | 7/2010 |
| JP | 2011502615 A | 1/2011 |
| JP | 2011502734 A | 1/2011 |
| JP | 2011519082 A | 6/2011 |
| JP | 201237922 A | 2/2012 |
| JP | 2012520522 A | 9/2012 |
| JP | 2012527937 A | 11/2012 |
| WO | 9841267 A1 | 9/1998 |
| WO | WO-98/41267 A1 | 9/1998 |
| WO | 02058619 A2 | 8/2002 |
| WO | WO-02/058619 A2 | 8/2002 |
| WO | WO-2006/074251 A2 | 7/2006 |
| WO | WO-2007/118054 A2 | 10/2007 |
| WO | 2009067492 A1 | 5/2009 |
| WO | WO-2009/094293 A1 | 7/2009 |
| WO | 2009123769 A1 | 10/2009 |
| WO | 2010071187 A1 | 6/2010 |
| WO | 2010105010 A1 | 9/2010 |
| WO | WO-2011/073839 A2 | 6/2011 |
| WO | 2011139194 A1 | 11/2011 |
| WO | WO-2011/139194 A1 | 11/2011 |

OTHER PUBLICATIONS

Office Action issued in counterpart JP Application No. 2017-213870, dated Jul. 30, 2018.
Office Action issued in JP Application No. 2017-213870, dated Mar. 18, 2019.

\* cited by examiner

BREATHING APPARATUS AND METHOD FOR USER INTERACTION THEREWITH

This application is the U.S. National Phase Application of International Application No. PCT/EP2012/060454, filed Jun. 3, 2012. The disclosure of the above-mentioned International Application is hereby incorporated by reference in its entirety for all it discloses.

BACKGROUND OF THE INVENTION

1. Field of the Invention

This invention pertains in general to the field of breathing apparatuses. More particularly the invention relates to user interfaces of such breathing apparatuses.

2. Description of Prior Art

Breathing apparatuses are usually operated via a user interface comprising a number of dedicated hardware knobs and buttons. Lately, user interfaces that have a touch screen in addition to knobs and buttons have emerged.

An example of a breathing apparatus having a touch screen is disclosed in international patent application number WO 2011/139194 of the same applicant as the present application, which hereby is incorporated by reference in its entirety for all purposes. In WO 2011/139194 a user interface for a breathing apparatus is described that has a contact-sensitive screen operable to cause a change in the operation of the breathing apparatus based on touch input from an operator. The contact-sensitive screen has a first touch area through which a breathing apparatus setting can be changed by touch of an operator, and a second touch area at a distance from the first touch area. The user interface is configured such that the breathing apparatus setting can only be changed by touching said first and second touch areas simultaneously. Reference is made to graphical layout, scales, knobs etc. WO 2011/139194 deals with safety of user input by requiring that two points of a touch screen are to be simultaneously touched.

There is a need for providing alternatives, or further improving such user interfaces, in particular with regard to quick accessibility of adjustments of operational parameters, amongst others.

Hence, an improved breathing apparatus would be desired to be provided with an advantageously improved user interface.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a breathing apparatus, a method, and a computer-readable medium with instructions for a processor of a breathing apparatus, according to the appended patent claims.

Breathing apparatuses are for instance respiratory ventilators or anesthesia machines, including intensive care respiratory ventilators, home care respiratory ventilators or the like. The breathing apparatus provides in use a breathing gas to a subject which airways are fluidly connected to the apparatus. The apparatus may for instance in use be connected to sources of pressurized gas or be driven by a fan to provide the breathing gas. The breathing apparatus may also be a respiratory ventilator with anesthesia capabilities, e.g. based on volatile anesthetic agents. A touch screen of the breathing apparatus may be integrated with the apparatus or be provided in a separate unit or module, which directly or indirectly is in communication with the unit or module of the apparatus providing gas delivery control. However, it will be appreciated that the invention is not limited to a specific clinical application but may be applied to various breathing apparatuses, including for example all patient categories from neonatal to adult patients or veterinary applications.

According to one aspect of the invention, a breathing apparatus is provided.

The breathing apparatus may be any type of breathing apparatus for assisting breathing of a subject, such as an intensive care ventilator, an anesthesia machine, etc.

The breathing apparatus has one or more electronic processors and a touch screen communicatively coupled to at least one of the processors.

The touch screen is in embodiments a multi touch screen capable of recognizing the presence of two (dual touch) or more simultaneous points of contact with the surface thereof. The skilled person is able to recognize which type of touch screen is needed to implement specific kinds of touch based interaction of the present disclosure.

The processor is configured to provide a user interface on said touch screen for modification of at least one operational parameter of said breathing apparatus.

The term "operational parameter" of a breathing apparatus may include any common known respiratory parameters in the art. Operational parameters are adjustable for controlling the ventilator. Such parameters may be included in the following non-exhaustive list of parameters having a certain value during operation of the breathing apparatus: Oxygen (O2) content in inspiratory gases (O2 never less than 21%). Positive End Expiratory Pressure (PEEP), inspiratory pressure (Pinsp), tidal volume (Vt), Respiratory Rate (RR), etc. The operational parameters may also be comprised by any parameters previously edited by rotary knobs in breathing apparatuses. An example of such rotary knobs is described in U.S. Pat. No. 5,915,379, in particular with reference therein to FIG. 3, reference sign 106 and the description column 7, row 55 onwards. U.S. Pat. No. 5,915,379 is incorporated herein by reference in its entirety for all purposes.

The user interface may includes a display area with a toggle input element for toggling between different graphical representations, such as ranges or sizes, of touch based input elements.

Alternatively, or in addition, a pinch and zoom gesture may provide for changing ranges, like zoom in or zoom out ranges. The change of range may be done by the pinching movement of a pinch & zoom gesture. The pinch and zoom may be performed on a bar illustrating a first range which is changed to a second range of an operational parameter by the pinch & zoom. The bar may be a slider bar allowing for selecting a specific value or sub-range from the first or second range. In this manner, very quick selection of a coarse value for subsequent fine tuning is provided. It should be noted that subsequent fine tuning may be made in the second range, if zoomed in from the first range. Several zoom & pinch gestures may be performed for drilling down into narrower ranges and/or going to wider ranges, as desired by the operator.

In some embodiments, the user interface includes at least two touch sensitive display areas on the display area of the touch screen for modification of the operational parameter by an operator of the breathing apparatus. Each of the two touch sensitive display areas is dedicated for different types of user interaction, i.e. different user interaction modes are provided for by each of the two different display areas. This allows the operator for instance to choose one of the different types of user interaction particularly well suited for a certain clinical situation. Thus, an operational parameter may advantageously be adjusted in an efficient way. Operational safety may thus be increased, in particular in clinical environments where focus can be directed on treatment of the patient.

In some embodiments, a first interaction mode is a touch based stepwise modification mode. For this purpose, a first display area of the interface comprises first input elements for stepwise modification of the operational parameter upon user touch within the first display area. Stepwise modification may allow for a very precise, while quick, adjustment of a value of an operational parameter. Overshooting certain desired values to be adjusted is limited and entering or adjusting of operational parameters is provided efficiently in certain clinical situations.

In some embodiments, a second interaction mode is a touch based gradual modification mode. A second display area of the interface includes second input elements for gradual modification of the operational parameter. Alternatively, or in addition, the second input elements are provided for selection of a particular value from a range of the operational parameter upon user touch within the second display area.

In some embodiments, the second input elements comprise a slider bar for a range of the operational parameter. In particular embodiments the slider bar may include one or more visual indications of the following kind. A slider bar allows for a quick adjustment of a value within a range of values of an operational parameter. Thus, an operational parameter may advantageously be entered of adjusted in an efficient way. Operational safety may thus be increased.

The slider bar may include a visual indication of a current value of the operational parameter before modification. This may for instance be provided such as by means of an arrow and/or a numeric value at a position of the slider bar.

The slider bar may include a visual indication of a range between a lower and an upper limit of the operational parameter. This may for instance be provided such as by means of a color coded portion of the slider bar. This provides for a quick identification of selectable values and correlation to clinically preferred values within a range for an operator. Operational safety may thus be increased.

The slider bar may include a visual indication of a threshold value on the slider bar for indication of a clinically unusual value. This may for instance be provided such as by means of a number with a different color or shade than other numbers displayed along a range. This may alternatively or additionally for instance be provided such as by means of a number with a background color box. This may for instance be provided such as by means of a line in a different color or shade than other parts of the range along the slide bar. This may for instance be provided such as by means of orange numbers or lines. Providing a threshold value on a slider bar with selectable values within a range of values provides for a quick identification of selectable values and correlation to clinically preferred values within a range for an operator. Operational safety may thus be increased.

The slider bar may include a visual indication when the threshold value is passed, e.g. exceeded or subsided, upon user input, on the slider bar a sub-range adjacent the clinically unusual value in a different color or shade than other parts of the range. Surpassing of a threshold value may immediately be indicated during adjustment or thereafter, e.g. before a confirmation of a modified value. Operational safety may thus be increased as the operator gets a quick information.

In some embodiments, the user interface including a display area adjacent the second display area for providing information related to sub-ranges or limits of the operational parameter. Operational safety may thus be increased.

In some embodiments, the interface comprises a display area with a toggle input element for toggling between different graphical representations, such as ranges or sizes, of the second input elements upon user touch of the toggle input element. Operational safety may thus be increased by a quick selection of representations.

In some embodiments, the different ranges comprise an expanded range and a sub-range thereof illustrated in the expanded range in a different color or shade for reversible magnification thereof upon the user touch of the toggle input element.

In some embodiments, at least one of the limits is user selectable.

In some embodiments, the second display area comprises a continuous graph of a range of values for the operational parameter, wherein the continuous graph has a non-linear scale)

In some embodiments, the user interface includes a display area for information data elements related to the operational parameter based on letters and/or symbols, such as a headline of the operational parameter and/or a warning text related thereto.

In some embodiments, the processor is configured to provide the modification only after the user has touched one of the touch sensitive display areas for a predefined time, when a threshold value of at least one operational parameter has passed a threshold value, and/or the processor is configured to trigger an acoustic warning when the threshold value is passed.

In some embodiments, one or more of the processors are operable to interact with a computer-readable storage medium in order to perform operations for providing user communication via the touch screen. The operations may comprise: receiving, while a current view is displayed on the touch screen, a first user touch input requesting that a user interface is displayed for modification of the operational parameter; displaying the user interface, the display areas thereof including: a first display area for modification of the operational parameter in a first touch based manner, a second display area for modification of the operational parameter in a second touch based manner, different from the first touch based manner, receiving, while the user interface is displayed, a second touch based user input requesting that the operational parameter be modified; modifying, in response to the second user input, the operational parameter to a modified operational parameter by touching the first or second display area.

In some embodiments, the display areas of the user interface comprise a third display area for acknowledging a modified operational parameter, and a fourth display area for cancelling the modified operational parameter; the operations comprising: confirming the modified operational parameter for continued operation of the breathing apparatus by touching the third display area, or aborting the modification without changing the operational parameter, such as by touching the fourth display area or in absence of a confirmation after a pre-determined time.

In some embodiments, the display areas of the user interface comprise a fifth display area for a numeric value of the operational parameter, wherein the numeric value is of the modified operational parameter, wherein the numeric value or and/or a background thereof is visually coded in dependency of the value within a range of the operational parameter; and/or the operations comprising displaying a numeric value of the operational parameter before modification, particularly in the second display area.

According to another aspect of the invention, a method of providing user communication in a breathing apparatus is provided. The method comprises providing an on-demand user interface on a touch screen of the breathing apparatus for modification of an operational parameter of the breathing apparatus, and providing at least two touch sensitive display areas on the user interface for user modification of the operational parameter in different user interaction modes for each display area, wherein the method is preferably performed without ventilating a patient, such as in standby mode of the apparatus, effecting modification of the operational parameter upon touching at least one of the display areas by a user.

In some embodiments, the method comprises receiving, while a current view is displayed on the touch screen, a first user touch input requesting that a user interface is displayed for modification of the operational parameter; displaying the user interface, the display areas thereof including: a first display area for modification of the operational parameter in a first touch based manner, a second display area for modification of the operational parameter in a second touch based manner, different from the first touch based manner, receiving, while the user interface is displayed, a second touch based user input requesting that the operational parameter be modified; and modifying, in response to the second user input, the operational parameter to a modified operational parameter by touching the first or second display area.

According to yet another aspect of the invention, a breathing apparatus is provided. The apparatus has a touch screen, the touch screen having a touch sensitive display area for displaying a user interface for modification of at least one operational parameter of the breathing apparatus, the user interface having an input element for gradual modification of the operational parameter or selection of a particular value from a range of the operational parameter upon user touch within the second display area. The apparatus further has a tactile element arranged on or at the touch screen at a position related to the input element of the user interface, According to a further aspect of the invention, a computer-readable storage medium having embodied thereon a computer program for processing by a computer is provided. The computer-readable storage medium has instructions stored thereon that when executed by one or more of the processors perform operations for providing user communication via a touch screen of a breathing apparatus. The instructions comprise: receiving, while a current view is displayed on the touch screen, a first user touch input requesting that a user interface is displayed for modification of the operational parameter; displaying the user interface, the display areas thereof including: a first display area for modification of the operational parameter in a first touch based manner, a second display area for modification of the operational parameter in a second touch based manner, different from the first touch based manner, receiving, while the user interface is displayed, a second touch based user input requesting that the operational parameter be modified; and modifying, in response to the second user input, the operational parameter to a modified operational parameter by touching the first or second display area.

Further embodiments are defined in the dependent claims, wherein features for the second and subsequent aspects of the invention are as for the first aspect mutatis mutandis.

Some embodiments provide for multiple ways of touch based input in the same user interface. One and the same parameter may for instance be changed in multiple ways of user interaction within the same user interface. This provides for a number of advantages and effects.

Embodiments provide for entirely touch based modification of parameter value for operating a breathing apparatus. No hardware knob is needed while maintaining operational safety, reliability, and patient safety. As the user interface is not locked to fixed hardware knobs, flexibility of operating a breathing apparatus is increased. A user friendly, intuitive operation of a breathing apparatus is provided. However, the provision of a hardware knob in certain embodiments of breathing apparatuses is not excluded per-se for performing certain actions for controlling the breathing apparatus. Alternatively, or in addition, a hardware knob may be provided in certain embodiments as a redundant backup for adjustment of operational parameters.

A breathing apparatus having a touch screen only and no knob or button, or at least a touch screen and a reduced or minimum number of buttons or knobs, may also provide for easier cleaning of the apparatus. This may be advantageous of hygienic aspects.

Some embodiments provide for variable scales, adaptable for different ventilation parameter's ranges. This may provide for improved precision both for indicating current values or ranges of operational parameters of a breathing apparatus and improved precision for inputting such values.

Some embodiments provide for a quick, but coarse adjustment of a value of operational parameters of a breathing apparatus, e.g. by a slider bar and touching a value within a range shown by the slider bar for setting the value. As an increased resolution is provided in this manner, improved fine adjustment is provided, e.g. with a slider. Subsequent a gradual fine tuning of the value may be done. The gradual fine tuning may for instance be provided by +/− buttons, up/down buttons, or the like.

Additionally, a confirmation by the operator may be required by the user interface to actually update continued operation of the breathing apparatus with a thus changed value of the operational parameter. This may be provided by means of a confirmation button. This provides for a safe adjustment, as it effectively prevents unintended adjustments made by mistake.

Hence, embodiments provide for a quick and reliable adjustment of operational parameters of a breathing apparatus.

Some embodiments of the invention also provide for increased safety when operating a breathing apparatus. Thanks to certain embodiments, it may be difficult for an operator of a breathing apparatus to select values for operational parameters that may not be optimal for patient treatment or patient safety. Some embodiments thus may effectively prevent an operator from selecting "extreme" or otherwise uncomfortable or unsuitable values of operational parameters of a breathing apparatus. Some embodiments may provide for "normal", secure ranges of operational parameters to be selectable only, or only without express user confirmation to go outside these secure ranges. This may provide experienced users with an improved degree of operational comfort and safety for modification of operational parameter values.

Hence, user comfort as well as patient safety is increased.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF PREFERRED EMBODIMENTS

Figure 1:
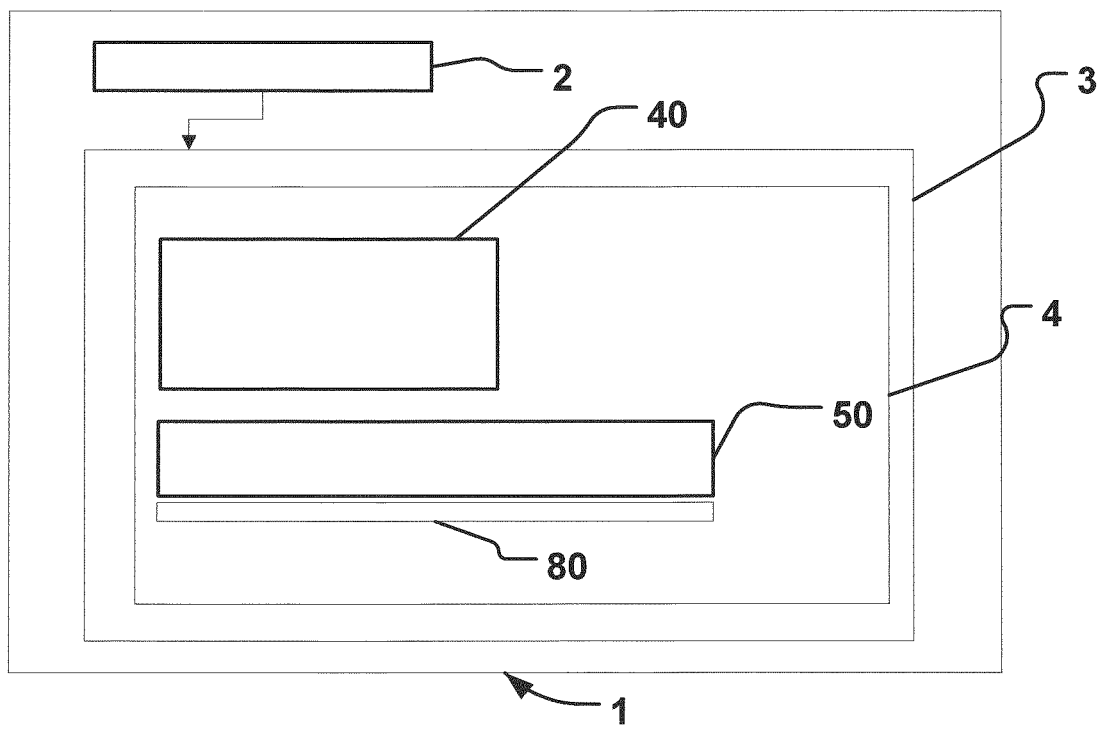
FIG. 1 is a schematic view of a breathing apparatus having a touch screen.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description describes embodiments applicable to a breathing apparatus.

Now turning to the figures, a breathing apparatus 1, as an example for implementing embodiments, is described with initial reference to FIG. 1.

The breathing apparatus 1 has one or more electronic processors 2 and a touch screen 3 communicatively coupled to at least one of the processors 2. The processor 2 is configured to provide a user interface 4 on the touch screen 3 for modification of at least one operational parameter of said breathing apparatus 1.

The user interface 4 includes at least two touch sensitive display areas 40, 50 on a total display area of the touch screen 4 for modification of the operational parameter by an operator of the breathing apparatus 1.

As illustrated in FIG. 1, a first touch sensitive display area 40 and a second touch sensitive display area 50 are provided on the touch screen.

Each of the two touch sensitive display areas 40, 50 are provided for different types of user interaction for the same operational parameter.

Different user interaction modes are provided for by each of the two different display areas 40, 50.

Although embodiments are generally shown with two different types of user interaction, other embodiments may comprise more than two different types of user interaction within the same user interface. Preferably, the two touch sensitive display areas 40, 50 are adjacent to each other, as illustrated in various embodiments below. The two touch sensitive display areas 40, 50 may be integrated into a single widget, e.g. within a frame or window on the touch screen. The different display areas may be provided in a separate window within a larger user interface. This kind of windows may be based on code similar to a software "widget", which is a stand-alone application to be embedded into larger software packages. The two touch sensitive display areas 40, 50 may be activated upon user selection.

Different types of user interaction will now be described in more detail.

Various user gestures may be performed by the operator of the breathing apparatus 1 by touching the touch screen with one or more fingers. In some embodiments of touch screens, instead of fingers, suitable pointer instruments like pens may be used. Capacitive detection based touch screens may advantageously only be operated by user's finger touch. In this manner, unintended operation of the breathing apparatus' touch screen may be advantageously avoided, e.g. merely touching the capacitive screen with clothes of clinical personnel will not result in any operational changes of the breathing apparatus.

Some user gestures are described hereinafter. However, the skilled person in the field will be aware of the available gestures for an operator of a touch screen.

A tap is for instance a short touch of a selected display area with a finger or other pointer instrument. In certain parts of the present disclosure, a tap allows e.g. for selecting a specific value from a range on a slider bar or activating a +/− button to incrementally change a value of an operational parameter.

A tap & hold is a touch of a selected display area without immediately removing the finger from the selected display area. A tap & hold allows e.g. for opening of context menu windows, etc. A pan is a user gesture where a finger is put on a selected display area of the touch screen 3 and kept in contact with the screen while moving around the display area thereof.

A pan allows e.g. for moving a selected range of values within a larger range on a slider bar without changing the span of the selected range of values. A double tap is user gesture where two taps are made quickly after each other.

A pinch is another user gesture where two fingers, like the thumb and index finger, are put on the screen at the same time and moved together sliding over the screen surface, in a pinching movement. A pinch may be used for changing ranges, like zoom in or zoom out ranges, e.g. as a gesture on a slider bar, implementing a pinch&zoom gesture.

In some embodiments, a first interaction mode is a touch based stepwise modification mode. This is described with reference to e.g. FIG. 4A, 4B, 5A, 5B, 6,7A-C, 9A, or 9B. For this purpose, a first display area 40 of the interface comprises first input elements 70 for stepwise modification of the operational parameter 6 upon user touch within the first display area.

To this end, first input elements are provided on the user interface 4 within a first display area 40.

Figure 4A:
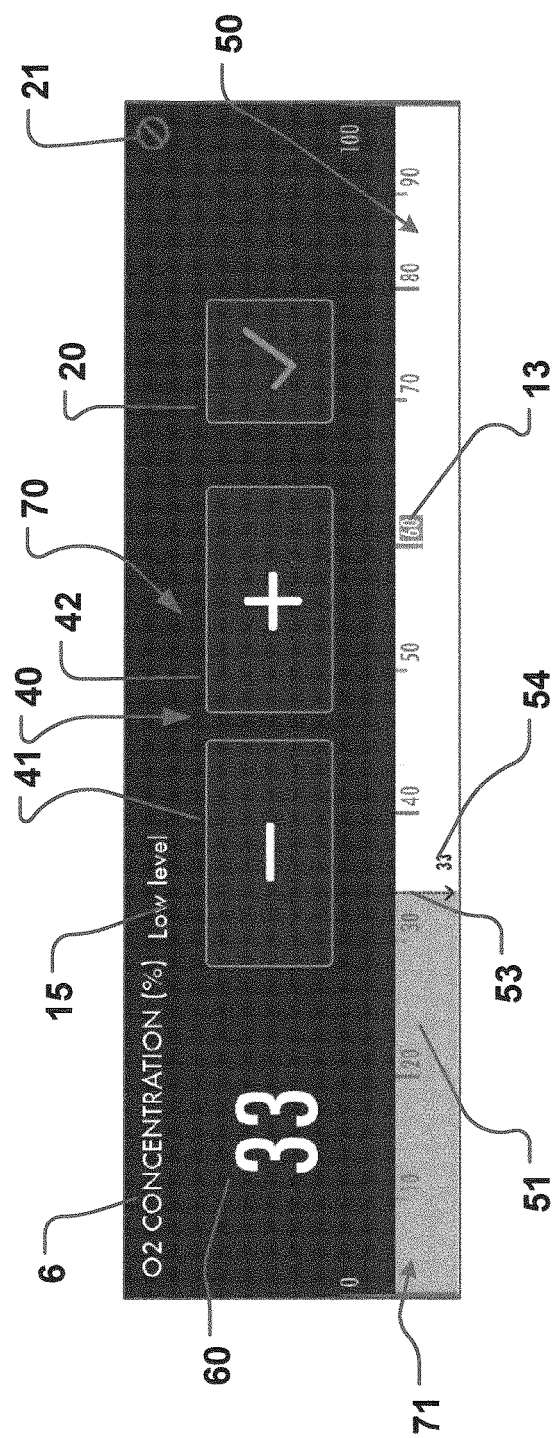
FIGS. 4A, 4B, 5A, 5B, 6, 7A, 7B, 7C, 8A, 8B, 8C, 9A and 9B are illustrations of examples of graphical user interfaces for parameter modification in a breathing apparatus.
Figure 4B:
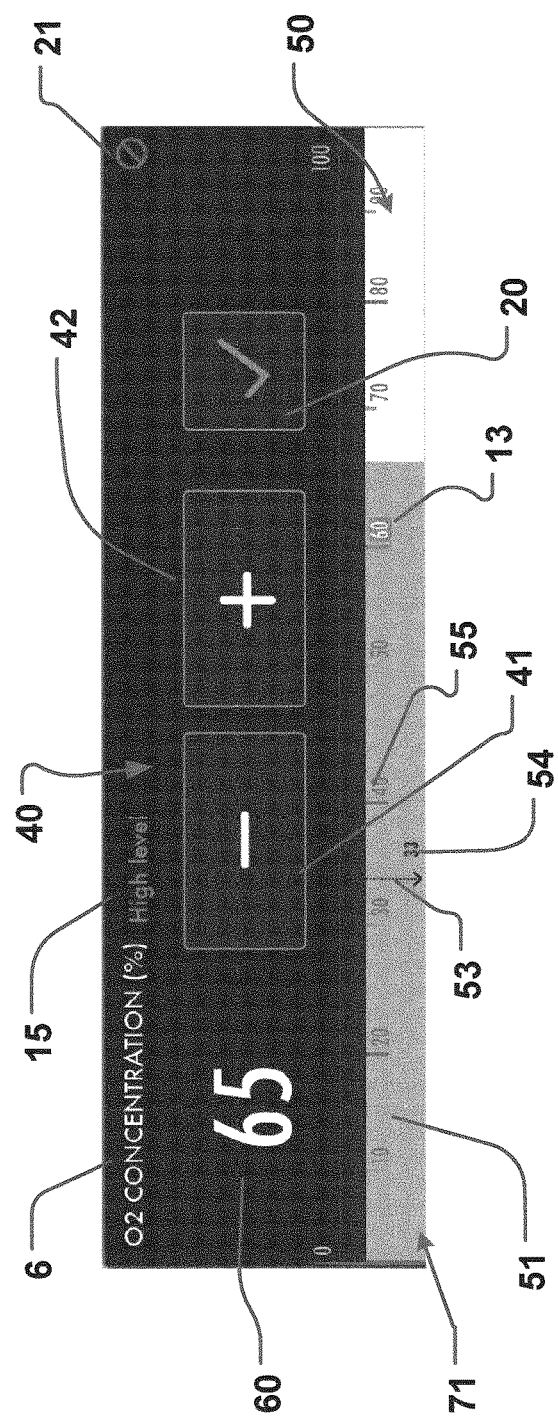
Figure 5A:
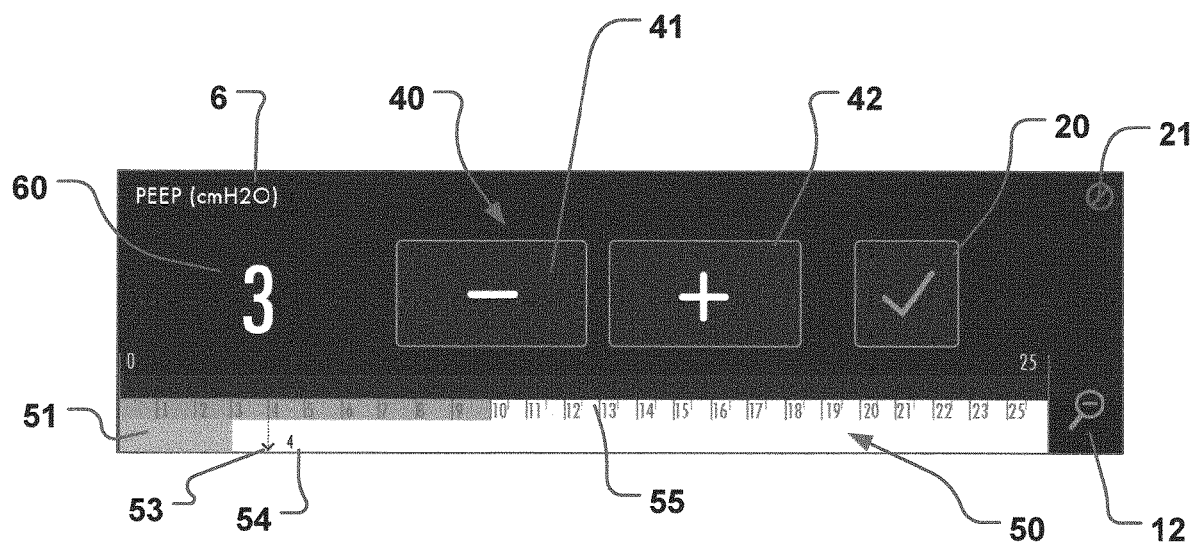
Figure 5B:
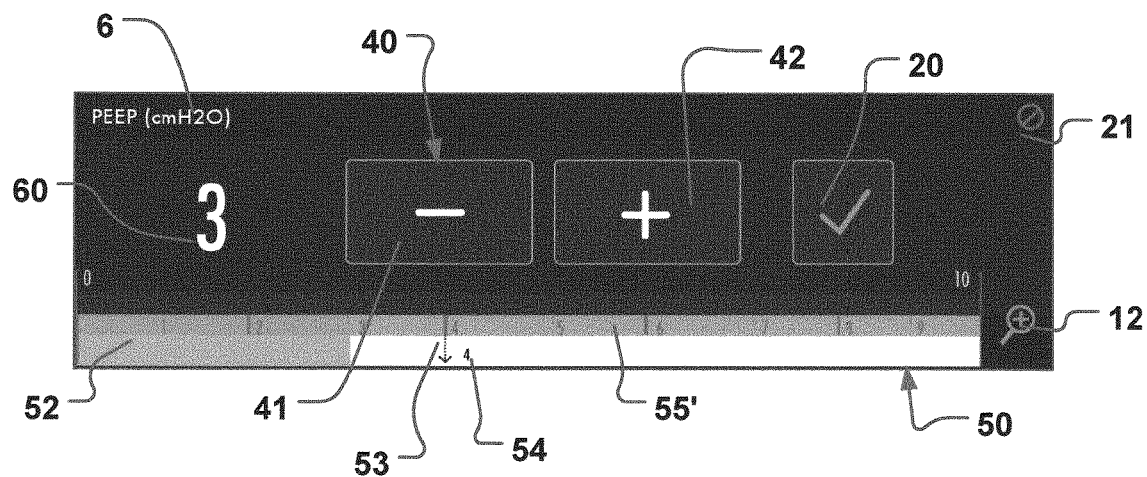

In the illustrated embodiments, two buttons 41, 42 are provided. A first button 41 is a "−" button for selecting a reduction, i.e. a downward change of the operational parameter 6. In FIGS. 4A, 4B, the operational parameter 6 is in an example illustrated as a O2 CONCENTRATION of an inspiratory breathing gas. A second button 42 is a "+" button for selecting an increase, i.e. an upward change of the value 60 of the operational parameter 6. In this manner, a stepwise increasing or decreasing change of the operational parameter 6 value 60 is provided for each tap on one of the +/− buttons 41, 42. By using a Tap and Hold a scroll mode may be entered where discrete values are changed in a sequence. A continuous Hold will accelerate the increase/decrease of value. The stepwise modification may be performed on integer values of the operational parameter. Alternatively, or in addition, decimal values may be stepwise modified by means of buttons 41, 42. The gradual fine tuning may for instance be provided by +/− buttons, as described above. Alternatively, up/down buttons, or the like may be provided.

In embodiments, a further interaction mode is provided by means of the user interface. In the illustrated embodiments a second interaction mode is a touch based gradual modification mode. A second display area 50 of the user interface 4 includes second input elements 71 for gradual modification of the operational parameter. Alternatively, or in addition, the second input elements 71 are provided for selection of a particular value from a range of the operational parameter upon user touch within the second display area.

The second input elements 71 may comprise an interaction slide bar, here illustrated and described as slider bar for a range of the operational parameter, as illustrated in the Figures. The slider bar lets the operator quickly select a specific value from a range of values via touch events on the second display area 50 on which the slider bar is shown.

The slider bar may provide for a plurality of user interaction modes. One is a direct access mode including tapping on a value within the range. Another is a slide access along the range.

The minimum and maximum values may be dynamically changed as will be described below.

The slider bar may allow for selection of a specific value within the range of values, which in certain embodiments may be compared to the operation of a rotary knob. Alternatively, or in addition, a slider bar may have a pre-defined step. The step size allows the operator to restrict the selectable values based on an incremental step, e.g. the operational parameter may be selectable as integer values only, or decimal parts thereof. The second display area may display tick marks and labels along the range. This is illustrated in the Figures and allows for a quick selection of a value in a certain area of a range visualized by the slider bar.

The operator may choose a specific value for the operational parameter 6 by touching slider bar at the region of the specific value, e.g. by a tap gesture. The current value of the operational parameter 6 will then be changed to a modified value to be confirmed by the operator, see the difference between FIG. 4A and FIG. 4B. Alternatively, the operator may choose to touch the slider bar at the current value, at an end of the bar 51, e.g. by a Tap and drag or panning gesture, and then drag the current value along the slider bar to the new, modified value. The bar graph follows to the modified value.

In this manner, a quick selection of a modified value for an operational parameter may be done based on the described use of the second input elements 71.

The modified value may be further modified, e.g. by fine tuning via buttons 41, 42.

Both when the quick selection of a modified value for an operational parameter is done in interaction modes of direct access or slide access, the fine tuning may be done subsequently.

One or both end points of current range may be changed by tapping or sliding. Alternatively, an entire range of values (bar) may be marked and grabbed, e.g. by a double tap, or by a tap & hold. Such a marked and grabbed sub-range may then be touch based moved in its entirety upward or downward, e.g. by panning.

Alternatively, a slider bar may be used for the first, gradual, modification mode: Tap on right of current value increases operational parameter value one step; Tap on left of current value decreases one step.

A slider bar may change input mode—providing both a first quick, but coarse mode and then a fine tuning mode. The input mode may be changed in various ways, e.g. by using a toggle element, or a pinch & zoom gesture.

The second input elements 71 may alternatively have other shapes as the illustrated linear slider bar. The second input elements 71 may be provided as graphical representations being curved or circular instead of straight, or straight along certain parts only and curved at other parts. Examples can be found in WO 2011/139194 of the same applicant, which is incorporated herein by reference in its entirety for all purposes.

An example for a circular input element is now described. The second input elements 71 may for instance be provided in the form of a touch based virtual rotary knob (not shown) with similar functionality. The virtual rotary knob may be operated by a circular tap and hold gesture. Visualization of a range may be made as a circular graph. Alternatively, or in addition, the rotary knob may be filled dependent on the selected value within a range, in a similar manner as a bar graph can be used to illustrate selected values. In terms of the virtual rotary knob, the circle of the knob may be filled in dependence of the currently selected value. Filling of a circle to illustrate values is for instance described in U.S. Pat. No. 5,931,160, in particular with reference to FIG. 5 thereof. An acknowledgement or confirmation of a selected or modified value may be done by "pressing" the virtual rotary knob, i.e. for instance a tap or double tap gesture within the display area of the virtual rotary knob.

The modified value of the operational parameter is preferably displayed within the display area comprising the first and second input elements, or adjacent thereto within a window, such as illustrated in FIGS. 4A, 4B, 5A, 5B, 6, 7A, 7B, 7C, 8A, 8B, 8C, 9A and 9B. The modified value may then be used by processor 2 for continued operation of the breathing apparatus 1. Before continued operation based on a modified operational parameter, it may in embodiments need to be confirmed by the operator in a further user input confirmation step. Confirmation accepting new settings may for instance be made by pressing a confirm button 20.

Alternatively, a modified value for an operational parameter may not be used for continued operation of the breathing apparatus 1. In this case, operation of the breathing apparatus 1 is continued with the unmodified, current value thereof.

Any modifications made need in embodiments be confirmed by the operator. If no confirmation is received, the modified value is not accepted. Alternatively, or in addition, a non-confirmation of the modified value, or an active abortion of the modification process will lead to the continued operation of the breathing apparatus 1 with the unmodified, current value of the operational parameter. A non-confirmation may be provided upon expiry of a predefined time limit within which no explicit confirmation of a modified value has been done by the operator. Alternatively, the modification may be actively canceled by the operator. This may for instance be done by tapping a cancel button, like a close button 21 illustrated in the Figures.

In particular embodiments the second input elements 71, e.g. the illustrated slider bar, may include one or more visual indications of data of the breathing apparatus to be communicated to the operator.

The second input elements 71, e.g. the illustrated slider bar, may include a visual indication of a current value of the operational parameter 6 before modification. This may for instance be provided such as by means of an arrow 53 and/or a numeric value 54 at a position thereof at the second input elements 71, e.g. the illustrated slider bar. The current value before modification may be shown at the position of the current value within a range, as shown in the Figures.

The second input elements 71, e.g. the illustrated slider bar, may include a visual indication of a range between a lower and an upper limit of the operational parameter. This may for instance be provided such as by means of a color coded portion 58 of the second input elements 71, e.g. the illustrated slider bar, see e.g. FIG. 6.

The second input elements 71, e.g. the illustrated slider bar, may include a visual indication of a threshold value 13 for indication of a clinically unusual value; see e.g. FIGS. 4A, 4B, 6, 7A-C, 8A-C, 9A and 9B. This may for instance be provided such as by means of a numerical value displayed with a different color or shade than other numbers displayed along a range. This threshold indication may alternatively or additionally for instance be provided such as by means of a number with a background color box, see e.g. FIGS. 4A, 4B, 6, 7A-C, 8A-C, 9A and 9B. This threshold indication may for instance be provided such as by means of a line in a different color or shade than other parts of the range along the slide bar, see e.g. FIGS. 4A, 4B, 7A-C, 8A-C, 9A and 9B. This threshold indication may for instance be provided such as by means of orange numbers or lines, see e.g. FIGS. 4A, 4B, 6, 7A-C, 8A-C, 9A and 9B.

Figure 8A:
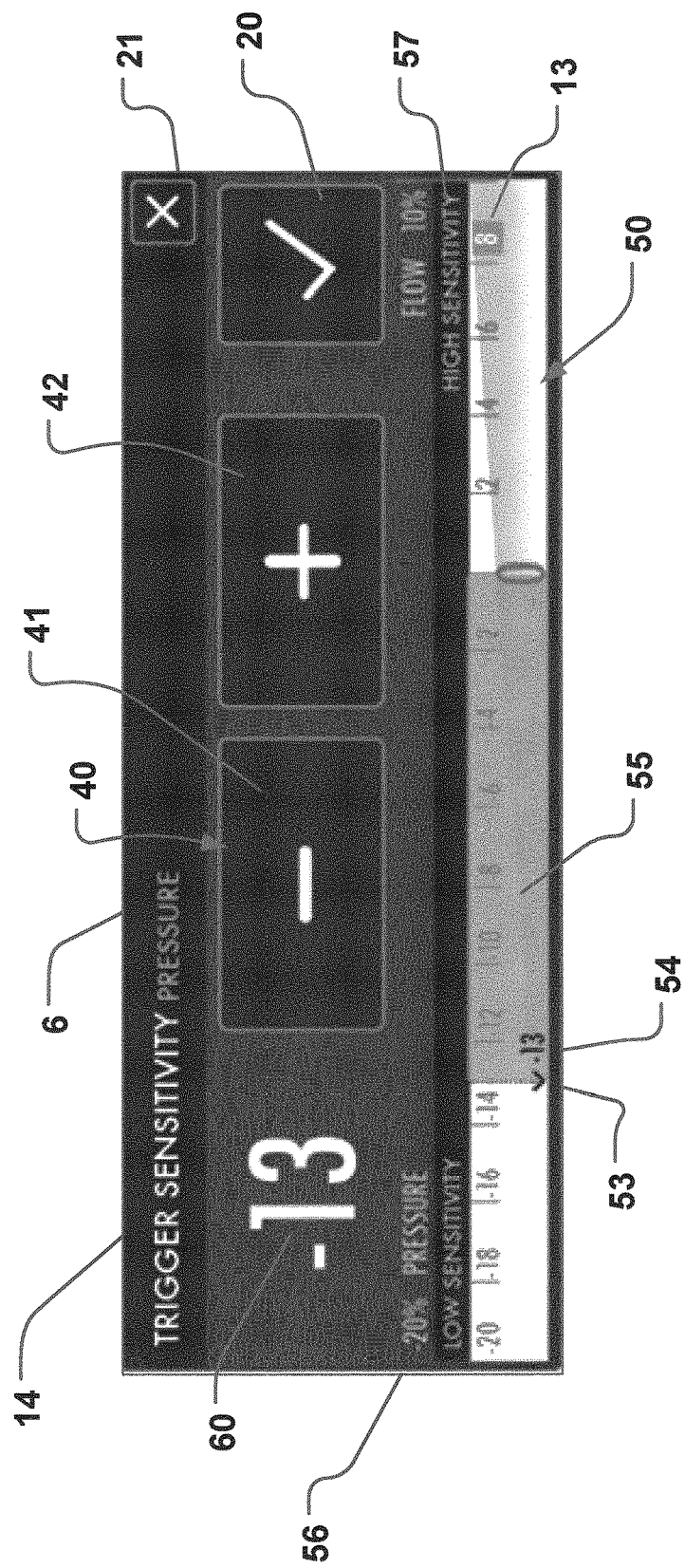
Figure 8B:
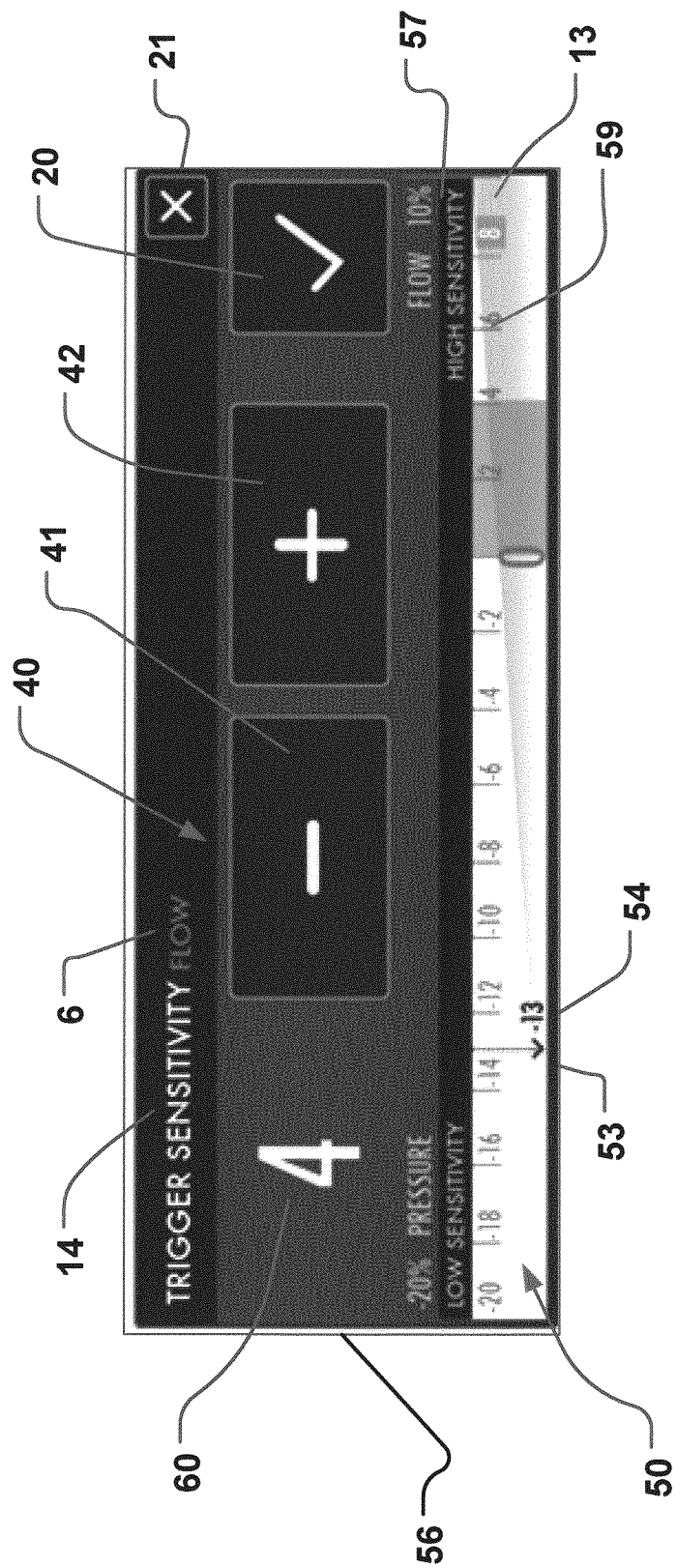
Figure 8C:
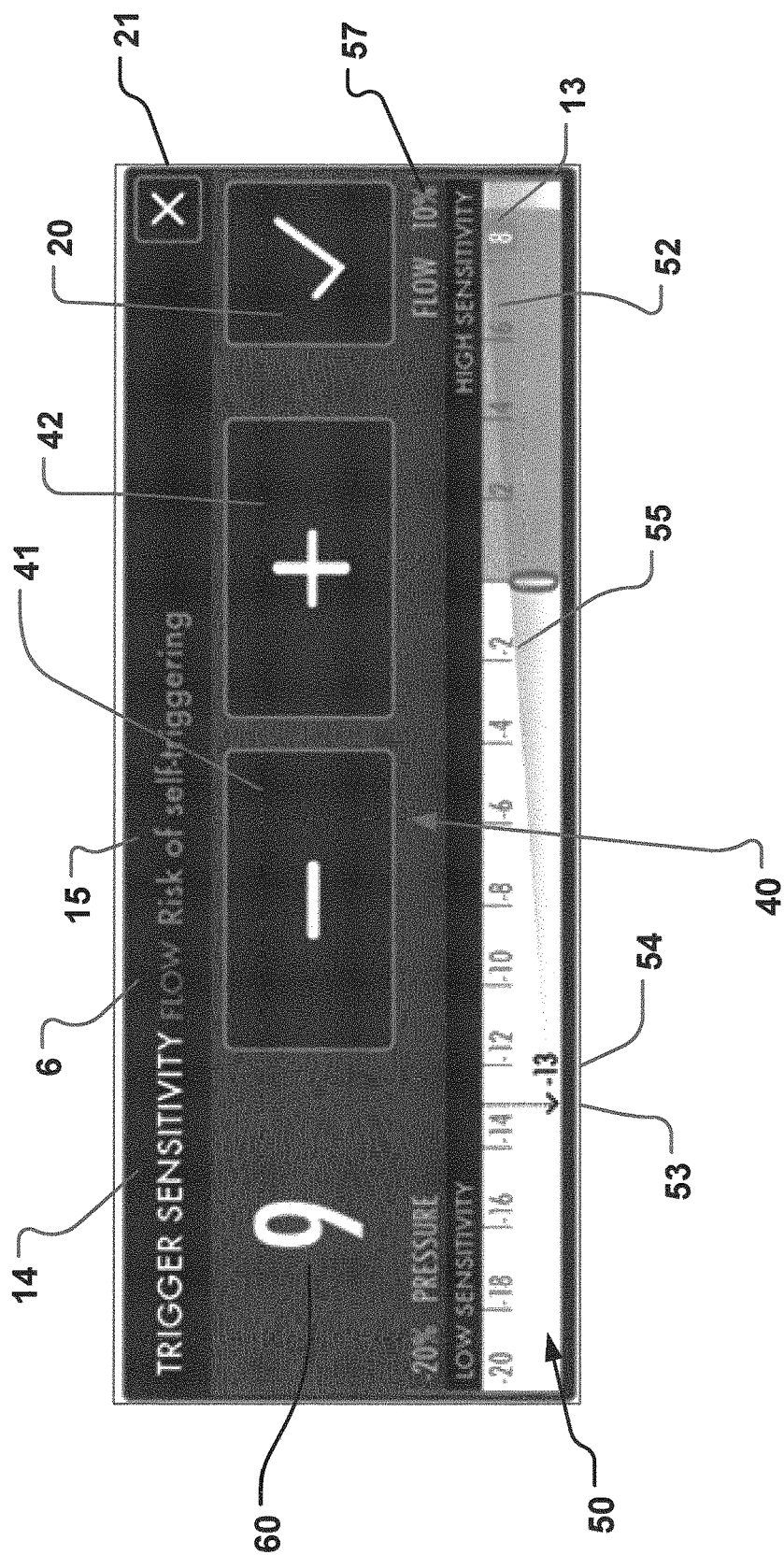
Figure 9A:
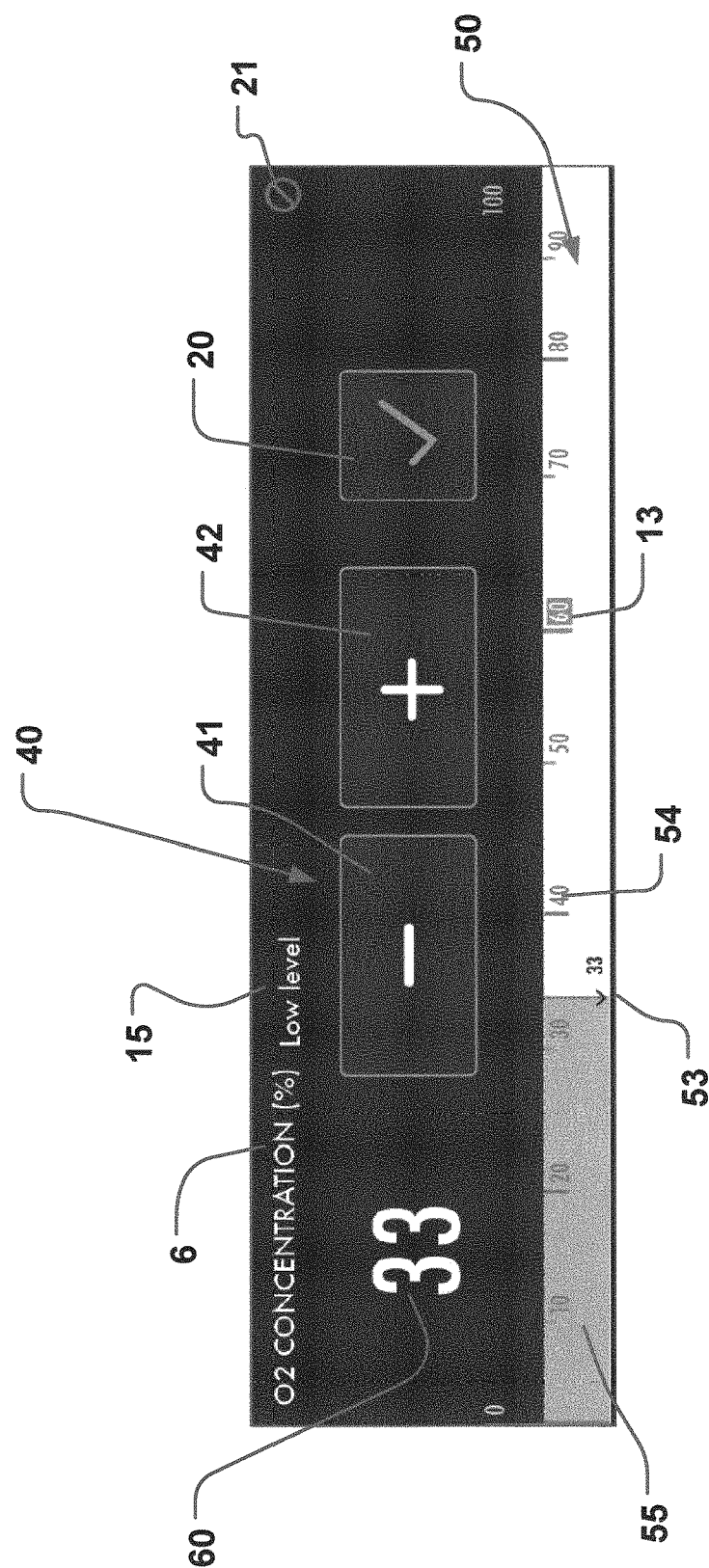
Figure 9B:
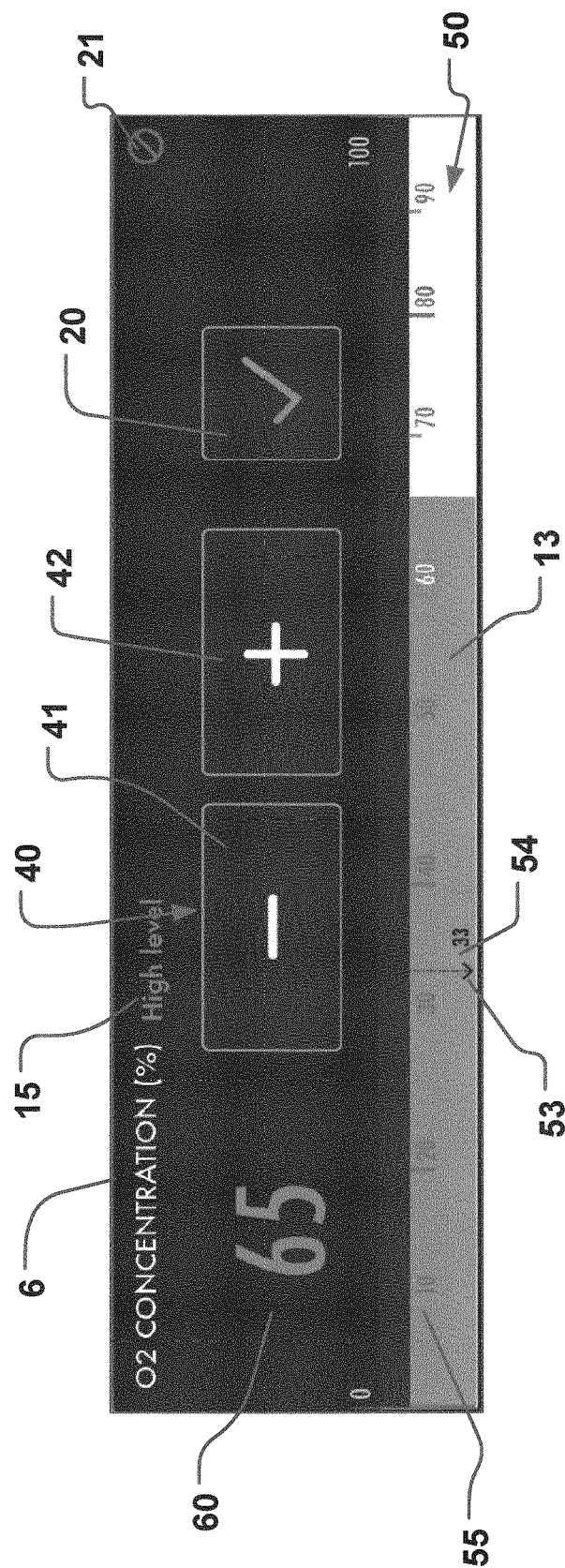

The second input elements 71, e.g. the illustrated slider bar, may include a visual indication when the threshold value is passed, e.g. exceeded or subsided, upon user input, on the second input elements 71, e.g. the illustrated slider bar, a sub-range adjacent the clinically unusual value in a different color or shade than other parts of the range, see e.g. FIG. 8C.

In some embodiments, the user interface may include a display area adjacent the second display area for providing information related to sub-ranges or limits of the operational parameter, see e.g. FIGS. 6, 7A-C, and 8A-C. For instance a range 55 is illustrated between a lower and an upper limit of operational parameter. A first information text 56 is illustrated on the left end of the slider bar left. A second information text 57 is illustrated at the right end of the slider bar. Further, a color-coded portion 58 with a first color change is shown. Also, a second color-coded portion 59 with a second color change is shown.

Figure 6:
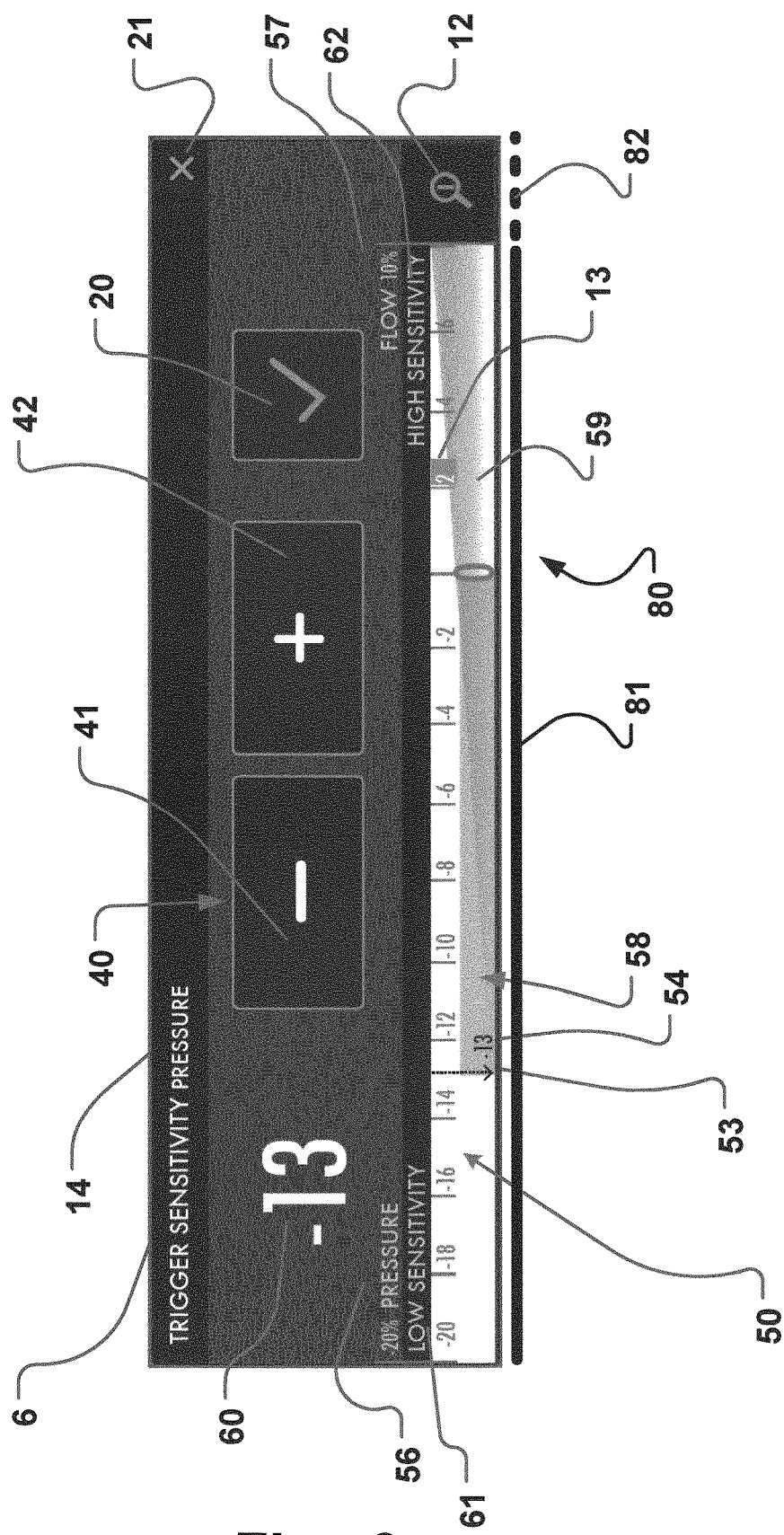
Figure 7A:
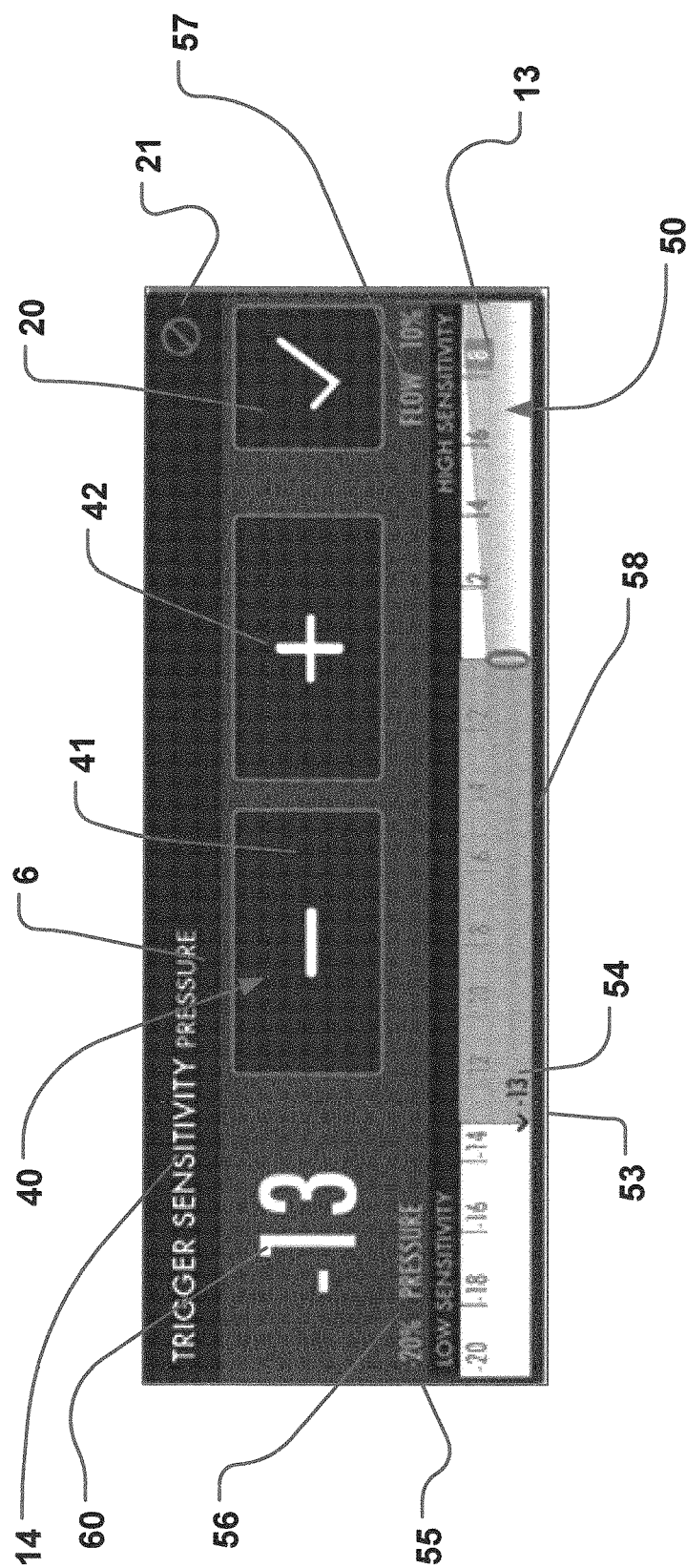
Figure 7B:
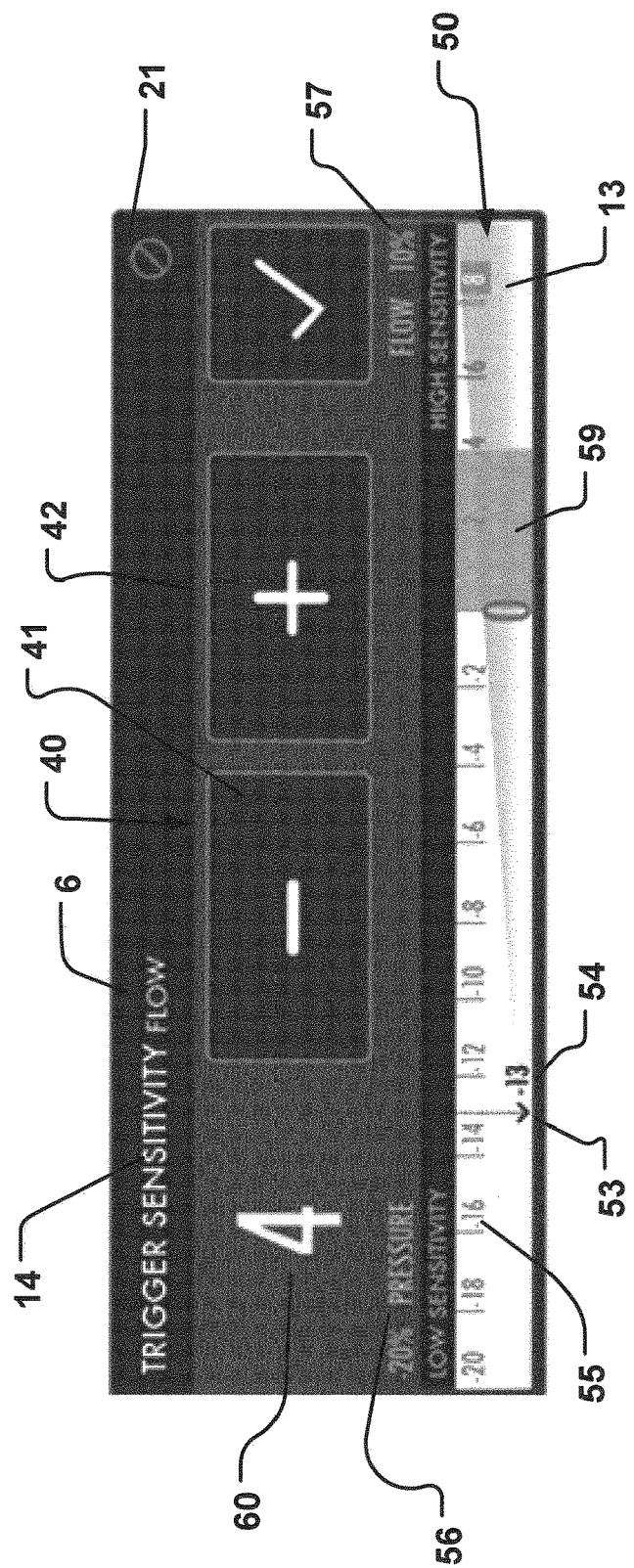
Figure 7C:
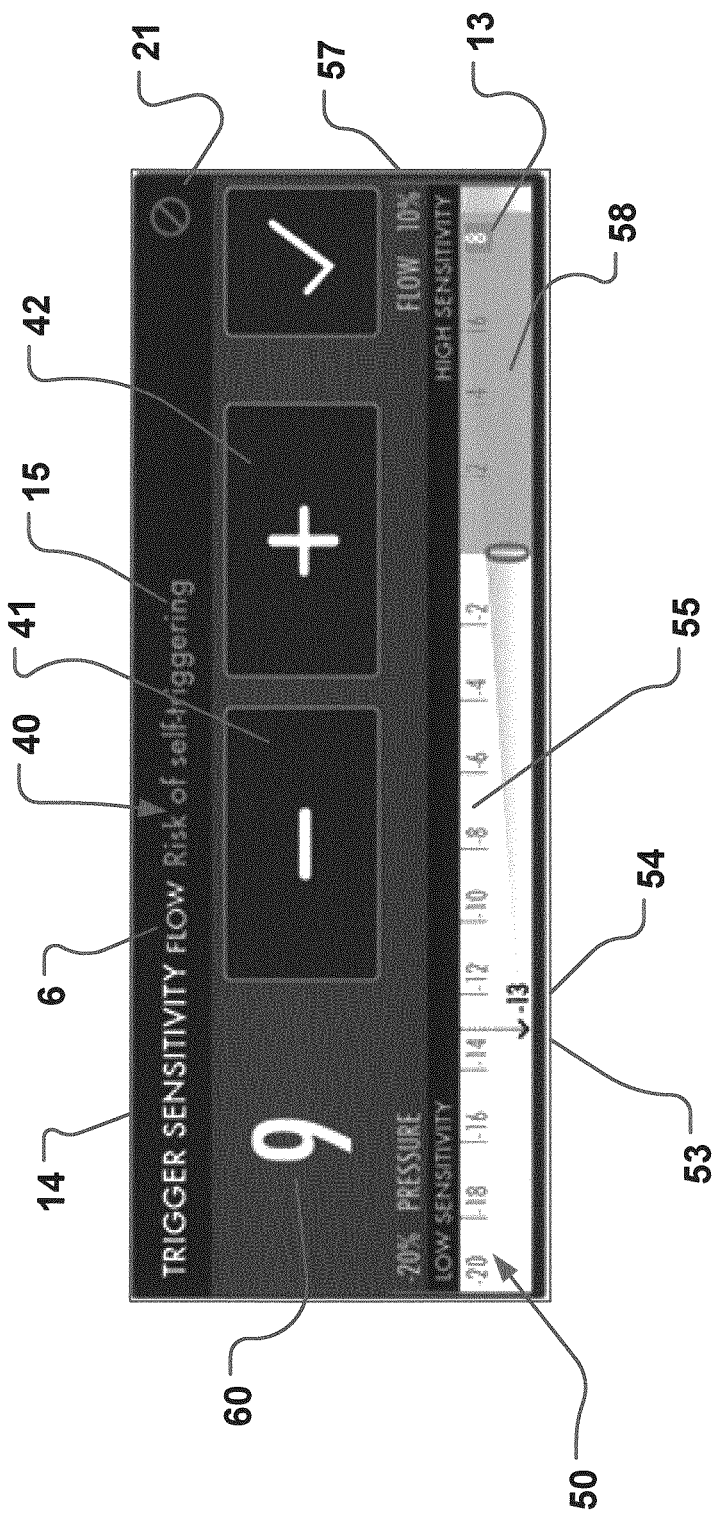

This informative bar (above) may provide additional information related to second input elements 71, e.g. the illustrated slider bar. In this manner the operator is supported and input of operational parameters made reliable and safe. An example of such additional information is e.g. the first text 61 "low sensitivity" shown at lower values of a range and/or the second text 62 "high sensitivity" shown at a position of higher values of a range, as shown in FIG. 6. In FIG. 6 a wedge shaped bar 59 is shown illustrating another example of graphical support for the operator. The wedge shaped bar increases in height with increasing values of the range or a sub-range of the slider bar in the second touch sensitive display area 50.

The user interface 4 may include a display area with a toggle input element 12 for toggling between different graphical representations, such as ranges or sizes, of touch based input elements. See e.g. FIGS. 5A and 5B.

Upon user touch of the toggle input element 12, e.g. by a tap gesture, toggling (switching) between different graphical representations is executed by processor 2.

In some embodiments, the different ranges comprise an expanded range and a sub-range thereof illustrated in the expanded range in a different color or shade for reversible magnification thereof upon the user touch of the toggle input element.

Alternatively, or in addition to a toggle element, a pinch and zoom gesture may provide for changing ranges, like zoom in or zoom out ranges. The change of range may be done by the pinching movement of a pinch & zoom gesture. The pinch and zoom may be performed on a bar illustrating a first range which is changed to a second range of an operational parameter by the pinch & zoom. The bar may be a slider bar allowing for selecting a specific value or sub-range from the first or second range. In this manner, very quick selection of a coarse value for subsequent fine tuning is provided. It should be noted that subsequent fine tuning may be made in the second range, if zoomed in from the first range. Several zoom & pinch gestures may be performed for drilling down into narrower ranges and/or going to wider ranges, as desired by the operator.

In some embodiments, at least one of the limits of a range is user selectable. For instance an upper and/or lower limit for a range of normal or secure range of values is user selectable.

In some embodiments, the second display area comprises a continuous graph of a range of values for the operational parameter, wherein the continuous graph has a non-linear scale (not shown). This allows for an improved illustration of "normal range" within total range).

Less frequent used value ranges, including both upper and/or lower ranges, may be hidden or deactivated to further improve precision for selecting vales for operational parameters 6. This is particularly advantageous for parameters including Oxygen content in inspiratory gases (02 never less than 21%), Positive end expiratory pressure (PEEP), and inspiratory pressure (Pinsp)

In some embodiments, the user interface includes a display area for information data elements related to the operational parameter 6 based on letters and/or symbols, such as a headline of the operational parameter and/or a warning text 15 related thereto. For instance a text like a headline of a window for modifying an operational parameter of a breathing apparatus may comprise a text describing the parameter to be adjusted with words and/or symbols. Alternatively, or in addition, the information data elements may comprise a warning text. A warning text may for instance be shown when a threshold limit for non normal values of an operational parameter is exceeded, e.g. a colored text in a headline. Examples are shown in the Figures., e.g. "High level", "Potential self triggering" etc. The information data elements may also comprise a status of the breathing apparatus. A status may be "standby", "patient not connected", "upstart pre run check", "patient connected and apparatus operating", On/Off or activated/deactivated statuses of e.g. "tube compensation", "leakage compensation", etc. The information data elements may be displayed as text and/or graphical symbols. A modified operational parameter value may be highlighted, like color coded. Changes when a predefined non normal threshold value is exceeded may thus easily be recognized by the operator. A value might start to blink. A value might change color, e.g. from a convenient color like white or blue to an alerting color like orange or red.

This allows the operator to quickly perceive a status of the breathing apparatus 1 to be considered when modifying an operational parameter.

In some embodiments, the processor 2 is configured to provide the modification only after the user has touched one of the touch sensitive display areas for a predefined time, when a threshold value of at least one operational parameter has passed a threshold value. In some embodiments, the processor 2 is configured to provide a warning, such a visual or an acoustic warning when the operator selects a value of an operational parameter that exceeds a threshold value.

In some embodiments, the display areas of the user interface comprise a fifth display area for a numeric value of the operational parameter, wherein the numeric value is of the modified operational parameter, wherein the numeric value or and/or a background thereof is visually coded in dependency of the value within a range of the operational parameter; and/or the operations comprising displaying a numeric value of the operational parameter before modification, particularly in the second display area. An identical color may for instance be used for the numeric value and a slider bar to illustrate a clinically unusual value, as described above. Thus, the attention of the operator may be raised and operational safety of the breathing apparatus 1 be increased.

Figure 2A:
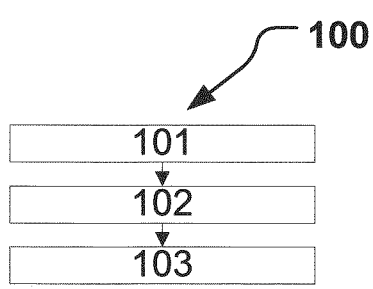
FIGS. 2A and 2B are flowcharts of methods.

FIG. 2A is a flowchart of a method 100.

According to another aspect of the invention, a method of providing user communication in a breathing apparatus is provided. The method comprises providing an on-demand user interface on a touch screen of the breathing apparatus for modification of an operational parameter of the breathing apparatus, and providing at least two touch sensitive display areas on the user interface for user modification of the operational parameter in different user interaction modes for each display area. The method may be provided in any operational modes of the breathing apparatus, e.g. when ventilating a patient for modification of a currently active operational parameter, for adjusting an operational parameter that is inactive in preparation for another breathing mode where the operational parameter is active, or in standby mode of breathing apparatus 1. This method may in an example be performed during operation of the breathing apparatus, i.e. ventilating a subject connected to the apparatus. In a particular embodiment the method is performed without a connected patient, or without ventilating a patient, such as in the standby mode of the breathing apparatus 1, effecting modification of the operational parameter upon touching at least one of the display areas by a user.

Figure 2B:
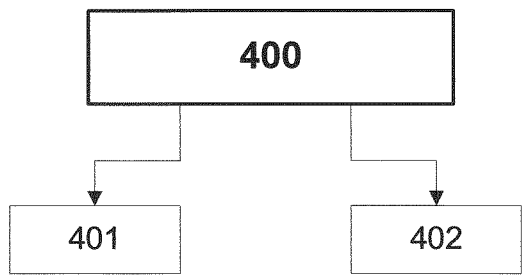

FIG. 2B is a flowchart illustrating an embodiment, in which a method 400 comprises receiving, while a current view is displayed on the touch screen, a first user touch input 401 requesting that a user interface is displayed for modification of the operational parameter; displaying the user interface, the display areas thereof including: a first display area for modification of the operational parameter in a first touch based manner, a second display area for modification of the operational parameter in a second touch based manner 402, different from the first touch based manner, receiving, while the user interface is displayed, a second touch based user input requesting that the operational parameter be modified; and modifying, in response to the second user input, the operational parameter to a modified operational parameter by touching the first or second display area.

According to a further aspect of the invention, a computer-readable storage medium having embodied thereon a computer program for processing by a computer is provided. The computer-readable storage medium has instructions stored thereon that when executed by one or more of the processors perform operations for providing user communication via a touch screen of a breathing apparatus. The instructions comprise: receiving, while a current view is displayed on the touch screen, a first user touch input requesting that a user interface is displayed for modification of the operational parameter; displaying the user interface, the display areas thereof including: a first display area for modification of the operational parameter in a first touch based manner, a second display area for modification of the operational parameter in a second touch based manner, different from the first touch based manner, receiving, while the user interface is displayed, a second touch based user input requesting that the operational parameter be modified; and modifying, in response to the second user input, the operational parameter to a modified operational parameter by touching the first or second display area.

Figure 3:
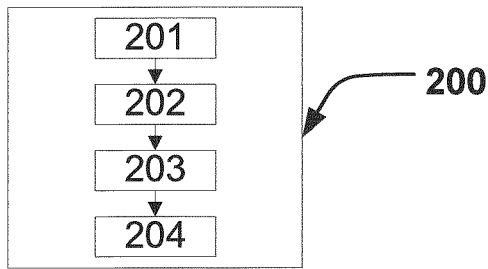
FIG. 3 is a schematic illustration of a computer readable medium having instructions stored thereon.

FIG. 3 is a schematic illustration of a computer readable medium 200 having instructions stored thereon.

In some embodiments, one or more of the processors are operable to interact with a computer-readable storage medium in order to perform operations for providing user communication via the touch screen. The operations may comprise: receiving, while a current view is displayed on the touch screen, a first user touch input requesting that a user interface is displayed for modification of the operational parameter; displaying the user interface, the display areas thereof including: a first display area for modification of the operational parameter in a first touch based manner, a second display area for modification of the operational parameter in a second touch based manner, different from the first touch based manner, receiving, while the user interface is displayed, a second touch based user input requesting that the operational parameter be modified; modifying, in response to the second user input, the operational parameter to a modified operational parameter by touching the first or second display area.

In some embodiments, the display areas of the user interface comprise a third display area for acknowledging a modified operational parameter, and a fourth display area for cancelling the modified operational parameter; the operations comprising: confirming the modified operational parameter for continued operation of the breathing apparatus by touching the third display area, or aborting the modification without changing the operational parameter, such as by touching the fourth display area or in absence of a confirmation after a pre-determined time.

According to yet another example, a breathing apparatus is provided. The apparatus has a touch screen, the touch screen having a touch sensitive display area for displaying a user interface for modification of at least one operational parameter of the breathing apparatus. The breathing apparatus may be of the type described afore. The user interface may includes an input element for gradual modification of the operational parameter or selection of a particular value from a range of the operational parameter upon user touch within the second display area.

The apparatus further has a tactile element 80 (see an example in FIG. 6) arranged on or at the touch screen. The tactile element 80 is arranged at a position related to the input element of the user interface. The tactile element 80 may be arranged on the screen surface of the touch screen. Alternatively, or in addition, it may be arranged adjacent the screen surface, e.g. on a frame of the touch screen.

The tactile element may be a protrusion, a recess, an area with a different surface roughness, etc., which is recognizable and distinguishable from other screen areas by tactile sensing.

The tactile element 80 may be an integral part of the touch screen surface. Alternatively, it may be attached to the touch screen surface or adjacent thereto.

The user will thus easily be guided to a specific screen area by the hardware tactile element 80. The hardware tactile element 80 may be arranged on the touch screen surface itself or adjacent to it, e.g. on a screen frame arranged around the display area of the touch screen instead of directly on the touch screen display area.

The hardware tactile element 80 provides for instance an ergonomic support for the finger of an operator sliding along an input element, such as a slider bar.

The hardware tactile element 80 is for instance aligned with the user interface second input elements 71, as illustrated in an example in FIG. 6. The hardware tactile element 80 may have several sections with different tactile feedback.

A first region 81 of the tactile element 80 may be provided as a continuous element, e.g. for sliding along a range of a slider bar. e.g. the illustrated slider bar. A second region 81 may be provided as a non-continuous element, e.g. for identifying the position of the toggling input element 12.

In a clinical environment, the hardware tactile element 80 may provide a very advantageous assistance to the operator, often using gloves that may even be covered by body fluids, surgical tissue parts, etc. making it difficult to find a certain display area on a flat display screen, or slipping unintentionally to display areas not desired.

The hardware tactile element 80 may be provided with an active feedback element. The active feedback element may provide the operator with guidance on input made by an active feedback.

The active feedback element may e.g. be an optical feedback. The optical feedback may be activation of an illuminating light source of the hardware tactile element 80. The hardware tactile element 80 may be optically transparent or opaque. It may be illuminated by the display of the touch screen suitably controlled by processor 2. The hardware tactile element 80 may comprise a light source for illumination thereof. The hardware tactile element 80 may be a light guiding protrusion. Illumination may be activated when a user touch at the hardware tactile element 80 is detected. Illumination may be activated upon exceeding a threshold value as described above. Illumination may be changed upon user touch or input. A color of illumination may be changed, such as for indicating certain events as for instance a threshold being exceeded.

The active feedback element of the hardware tactile element 80 may alternatively or additionally be provided with a haptic feedback, e.g. by vibration. Haptic feedback may e.g. be given when activating an input element, such as toggling input element 12. Haptic feedback may e.g. be given when modifying an operational parameter to a non normal value, etc. The hardware tactile element 80 may provide the haptic feedback. Alternatively, or in addition, the entire touch screen, or a portion thereof may include elements for providing the haptic feedback to the operator. Haptic feedback is controlled by processor 2.

Although modifications and changes may be suggested by those skilled in the art, it is the intention of the inventors to embody within the patent warranted heron all changes and modifications as reasonably and properly come within the scope of their contribution to the art. The present invention has been described above with reference to specific embodiments. For instance, the different features and steps of embodiments may be combined in other combinations than those described. The scope of the invention is only limited by the appended patent claims.

The invention claimed is:

1. A breathing apparatus comprising:
a respiratory ventilator or an anesthesia machine that provides a breathing gas to a subject; and
at least one processor and a touch screen communicatively coupled to said processor;
said processor configured to provide a user interface on said touch screen that enables modification of at least one operational parameter of said breathing apparatus, wherein said at least one operational parameter is selected from the group consisting of oxygen content in the breathing gas, positive end expiratory pressure, inspiratory pressure, tidal volume, respiratory rate, pressure trigger sensitivity and flow trigger sensitivity;
said user interface comprising a display including at least two simultaneously displayed touch sensitive display areas for user modification of said operational parameter, wherein each of the at least two touch sensitive display areas are configured to be responsive to different types of touch-based user interaction modes in order to provide modification of the same operational parameter, thereby producing a modified operation and parameter, and wherein modification of said same operational parameter is effected by touching any of said at least two touch-sensitive display areas;
wherein a first interaction mode, of said different types of touch-based user interaction modes, is a touch based stepwise modification mode, and a first display area of said interface comprises first input elements for stepwise modification of said operational parameter upon user touch within said first display area;
wherein a second interaction mode, of said different types of touch-based user interaction modes, is a coarse modification mode, and a second display area of said interface comprises second input elements for selecting a particular value, from a displayed range of values for said at least one operational parameter, upon user touch within said second display area, thereby modifying said at least one operational parameter more coarsely but more quickly than upon said user touch within said first display area, wherein the second input elements comprise a slider bar for the displayed range of said operational parameter, wherein the slider bar includes visual indications of a current value of said operational parameter before modification and at least one of
an operation range between a lower limit and an upper limit of said operational parameter; and
a threshold value on the slider bar for indication of a clinically unusual value, wherein when the threshold value is passed upon user input, on the slider bar a sub-range adjacent the clinically unusual value in a different color or shade than other parts of the operational range is displayed; and
said processor configured to display a variable scale in said user interface for said at least one operational parameter of the second interaction mode of said breathing apparatus, said variable scale having a total scale range, and said processor configured to adapt said variable scale to the operational range of said at least one operational parameter by hiding or deactivating at least one of an upper portion of said total scale range and a lower portion of said total scale range.

2. The apparatus of claim 1, wherein said user interface comprises a display area adjacent said second display area for providing information related to sub-ranges or limits of said operational parameter.

3. The apparatus of claim 1, wherein said user interface comprises a display area with a toggle input element for toggling between different graphical representations of said second input elements upon user touch of said toggle input element.

4. The apparatus of claim 3, wherein said different graphical representations comprise different ranges of displayed range of values, said different ranges being an expanded range and a sub-range thereof illustrated in said expanded range in a different color or shade for reversible magnification thereof upon said user touch of said toggle input element.

5. The apparatus of claim 1, wherein said processing unit is configured to expand or reduce a range shown on said display upon a pinch gesture at a display area of said display where said range is shown.

6. The apparatus of claim 2, wherein at least one of said limits is user selectable.

7. The apparatus of claim 1, wherein said second display area comprises a continuous graph of a range of values for said operational parameter, wherein said continuous graph has a non-linear scale.

8. The apparatus of claim 1, wherein said user interface comprises a display area for information data elements related to said operational parameter based on at least one of letters and symbols.

9. The apparatus of claim 1, wherein said processor is configured to provide said modification only after said user has touched one of said touch sensitive display areas for a predefined time, when a threshold value of at least one operational parameter has passed a threshold value.

10. The apparatus of claim 1, wherein said processor is configured to provide further display areas of said user interface, comprising a third display area for acknowledging a modified operational parameter, and a fourth display area for cancelling said modified operational parameter, and wherein said processor is configured to:
confirm said modified operational parameter for continued operation of said breathing apparatus upon detecting a touch at said third display area, to abort said modification without changing said operational parameter, upon detecting a touch at said fourth display area or in an absence of a confirmation during a predetermined time following producing said modified operational parameter.

11. The apparatus of claim 10 when said processor is configured to:
provide a fifth display area in said user interface, for a numeric value of said operational parameter, and to visually code at least one of said numeric value and a background thereof in dependency of a magnitude of said numeric value within a range of said operational parameter.

12. The apparatus of claim 10 wherein said operations comprise displaying a numeric value of said operational parameter before modification, in said second display area.

13. A breathing apparatus comprising:
a respiratory ventilator or an anesthesia machine that provides a breathing gas to a subject; and
a processor and a touch screen communicatively coupled to said processor;
said processor configured to provide a user interface on said touch screen that enables modification of at least one operational parameter of said breathing apparatus, wherein said at least one operational parameter is selected from the group consisting of oxygen content in the breathing gas, positive end expiratory pressure, inspiratory pressure, tidal volume, respiratory rate, pressure trigger sensitivity and flow trigger sensitivity;
said user interface comprising at least one displayed touch sensitive display area that permits user modification of said at least one operational parameter;
said processor configured to display, on said at least one display area, a touch-based input element that illustrates a range of selectable values for said at least one operational parameter, wherein the touch-based input element comprises a slider bar for the range of selectable values of said at least one operational parameter, wherein the slider bar includes visual indications of a current value of said at least one operational parameter before modification, an operational range between a lower limit and an upper limit of said at least one operational parameter, and a threshold value on the slider bar for indication of a clinically unusual value, wherein when the threshold value is passed upon user input, on the slider bar a sub-range adjacent the clinically unusual value in a different color or shade than other parts of the operational range is displayed; and
said processor configured to display a variable scale in said user interface for said at least one operational parameter of said breathing apparatus, said variable scale having a total scale range, and said processor configured to adapt said variable scale to an operational range of said at least one operational parameter by hiding or deactivating an upper portion of said total scale range and a lower portion of said total scale range.

14. The apparatus of claim 1, further comprising a tactile element arranged on or at the touch screen, wherein the tactile element is a protrusion, a recess or an area of surface roughness, wherein the tactile element is distinguishable from other areas of the touch screen by tactile sensing.

15. The apparatus of claim 14, wherein the tactile element comprises a light source for illumination thereof.

16. The apparatus of claim 15, wherein the tactile element further comprises a haptic feedback controlled by said processor so that the tactile element vibrates whenever the at least one operational parameter is modified to a non-normal value.

17. The apparatus of claim 1, wherein the first input elements are disposed above the slider on the display.

* * * * *